US007380550B2

(12) United States Patent
Sexton et al.

(10) Patent No.: US 7,380,550 B2
(45) Date of Patent: Jun. 3, 2008

(54) SYSTEMS AND METHODS FOR PARTICLE DETECTION

(75) Inventors: Douglas A. Sexton, La Jolla, CA (US); Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 692 days.

(21) Appl. No.: 10/768,865

(22) Filed: Jan. 30, 2004

(65) Prior Publication Data

US 2005/0166913 A1 Aug. 4, 2005

(51) Int. Cl.
*A61M 11/00* (2006.01)

(52) U.S. Cl. ............................ 128/200.14; 128/204.22

(58) Field of Classification Search ........... 128/200.14, 128/200.19, 200.23, 203.15, 204.21, 204.22, 128/205.23
See application file for complete search history.

(56) References Cited

U.S. PATENT DOCUMENTS 5,363,842 A * 11/1994 Mishelevich et al. .. 128/200.14
5,364,838 A 11/1994 Rubsamen
5,611,332 A 3/1997 Bono
5,630,409 A 5/1997 Bono et al.
5,672,581 A 9/1997 Rubsamen et al.
5,743,250 A 4/1998 Gonda et al.
5,842,468 A 12/1998 Denyer et al.
5,884,620 A 3/1999 Gonda et al.
5,894,841 A 4/1999 Voges
5,915,378 A 6/1999 Lloyd et al.
5,941,240 A 8/1999 Gonda et al.
6,062,212 A 5/2000 Davison et al.
6,125,844 A 10/2000 Samiotes
6,158,431 A 12/2000 Poole
6,167,880 B1 1/2001 Gonda et al.
6,196,218 B1 3/2001 Voges
6,269,810 B1 8/2001 Brooker et al.
6,325,475 B1 12/2001 Hayes et al.
6,390,453 B1 5/2002 Fredrickson et al.
6,443,146 B1 9/2002 Voges
6,546,927 B2 4/2003 Litherland et al.
6,598,602 B1 7/2003 Sjoholm
6,637,430 B1 10/2003 Voges et al.
2001/0037806 A1 11/2001 Scheuch et al.
2002/0026940 A1 3/2002 Brooker et al.
2002/0065685 A1 5/2002 Sasaki et al.
2002/0071871 A1 6/2002 Snyder et al.
2002/0092519 A1 7/2002 Davis (Continued)

FOREIGN PATENT DOCUMENTS

DE 41 05 190 A1 8/1992

(Continued)

*Primary Examiner*—Steven O. Douglas

(57) ABSTRACT

An inhalation system is disclosed that, in an exemplary embodiment, includes an ejector that ejects medicated droplets during an activation event, a conduit fluidically coupled to the ejector and configured to transport the droplets to a patient during an in-breath, and a particle detection system configured to determine whether the droplets have properly passed through the conduit and to the patient during an activation event. Also disclosed are methods for detecting particles in an inhaler system, with an exemplary method including generating a dose of medicament particles from an inhaler system; detecting particles emitted in the inhaler system; and determining if a desired particle flux has been achieved for inhalation by a patient.

27 Claims, 8 Drawing Sheets

U.S. PATENT DOCUMENTS

| | | |
|---|---|---|
| 2002/0195101 A1 | 12/2002 | Scheuch |
| 2003/0075171 A1 | 4/2003 | Jones et al. |
| 2003/0101991 A1 | 6/2003 | Trueba |
| 2003/0145853 A1 | 8/2003 | Meullner |
| 2003/0172929 A1 | 9/2003 | Meullner |
| 2003/0200964 A1 | 10/2003 | Blakely et al. |

FOREIGN PATENT DOCUMENTS

| | | |
|---|---|---|
| DE | 19845487 | 4/2000 |
| EP | 0570015 | 11/1993 |
| EP | 0729827 | 11/1994 |
| EP | 1211628 | 6/2002 |
| EP | 1293259 | 3/2003 |
| JP | 1070071 | 7/1989 |
| JP | 2002165887 | 6/2002 |
| WO | WO92/17231 | 10/1992 |
| WO | WO94/25259 | 11/1993 |
| WO | WO96/30643 | 10/1996 |
| WO | WO96/30645 | 10/1996 |
| WO | WO96/39257 | 12/1996 |
| WO | WO98/13601 | 4/1998 |
| WO | WO99/37347 | 7/1999 |
| WO | WO99/49919 | 10/1999 |
| WO | WO02/009574 | 7/2002 |

* cited by examiner

FIG. 3

```
         ┌──────────────────────┐
         │ 210                  │
         │ Patient activates    │
         │ device               │
         └──────────┬───────────┘
                    ▼
         ┌──────────────────────┐  ← 200
         │ 220                  │
         │ Aerosol generation   │
         │ starts               │
         └──────────┬───────────┘
                    ▼
         ┌──────────────────────┐
         │ 230                  │
         │ Particle detection   │
         │ activated            │
         └──────────┬───────────┘
                    ▼
         ┌ ─ ─ ─ ─ ─ ─ ─ ─ ─ ─ ┐
         │ 240                  │
         │ Inhalation starts    │
         └ ─ ─ ─ ─ ┬ ─ ─ ─ ─ ─ ┘
                   ▼
                 ◇ 250                      ┌────────────────┐
          Proper Particle ───────────────▶  │ 280            │
          Flux Detected?                    │ Device Fault   │
                 │                          │ Inferred       │
                 │                          └────────┬───────┘
                 ▼                                   ▲
         ┌──────────────────────┐                    │
         │ 260                  │          ┌─────────┴──────┐
         │ Aerosol generation   │          │ 290            │
         │ stops                │          │ Fault Response │
         └──────────┬───────────┘          └────────────────┘
                    ▼
         ┌ ─ ─ ─ ─ ─ ─ ─ ─ ─ ─ ┐
         │ 270                  │
         │ Exhalation starts    │
         └ ─ ─ ─ ─ ─ ─ ─ ─ ─ ─ ┘
```

FIG. 4

```
          ┌──310
          │ Patient Activates
          │     Device
          └──────┬───────┘
                 │   ┌──320
                 ▼
          ┌─────────────┐
          │  Aerosol Generation
          │      Starts
          └──────┬───────┘
                 │   ┌──330
                 ▼
          ┌─────────────┐
          │ Particle Detection
          │     Activated
          └──────┬───────┘
```

300

```
                 ┌──340
          ┌ ─ ─ ─┴─ ─ ─ ┐
          │  Inhalation  │
          │    Starts    │
          └ ─ ─ ─┬─ ─ ─ ┘
                 │   ┌──350
                 ▼
          ┌─────────────┐
          │   Aerosol
          │ Generation Stops
          └──────┬───────┘
                 │   ┌──360
          ┌ ─ ─ ─┴─ ─ ─ ┐
          │ Exhalation Starts
          │ and is Completed │
          └ ─ ─ ─┬─ ─ ─ ┘
                 │   ┌──370
                 ▼
             ◇ Full Dose ◇──── Indicate to Patient ──390
              Delivered?      Dosage Incomplete
                 │
                 │   ┌──380
                 ▼
          Indicate Dosage
          Complete to Patient
```

400 Update Calibration Factor

FIG. 5

SYSTEMS AND METHODS FOR PARTICLE DETECTION

BACKGROUND

For pulmonary delivery of aerosols and dry powders, delivered dose is difficult to predict and estimate. Deposition in the lungs is driven by numerous factors, including for example particle size, depth of inspiration, residence time, and lung condition.

Metered dose inhalers (MDIs), dry powder inhalers (DPIs), and nebulizers currently address the bulk of applications for pulmonary delivery of aerosols and dry powders. FDA guidance documents on MDIs and DPIs estimate that only about 10% -15% of dose reaches the biological target. The remainder is trapped in the mouth and pharynx and swallowed or is exhaled. Inhalers for delivering medicament to pulmonary systems historically can delivery fairly accurate amounts of inhalant in the form of an aerosol. More specifically, inhalers generally accurately generate a mist of inhalant for the patient to breathe into their pulmonary system. One issue is with whether the patient properly breathes in the inhalant being generated. A second issue is how much aerosol is expelled during an out-breath. Both issues will vary from patient to patient, making predictability and control of proper dosage difficult.

Delivery of particulates to the deep pulmonary regions of the lung, the alveoli, can be optimized by delivering particles of the proper size range and by increasing residence times. For alveoli deposition, particles with diameters in the range of about 1 to 3 microns appear optimal. Particles below approximately 3 microns in diameter have been shown, via scintigraphy studies, to be preferentially transported to the deep lungs, whereas larger particles tend strike the throat or rain out in the bronchial passages. Smaller particles penetrate more deeply but also have an increased tendency to be exhaled. Therefore, for deep pulmonary delivery systems exhalation of particles can be substantial issue.

Some devices for deep pulmonary delivery attempt to optimize delivered dose and delivered dose reproducibility by measuring inhalation and exhalation rates and delivering the drugs at critical points. While these small particle size systems with active measurement of breathing maneuvers should help to ensure more reproducible dosing, there are still many uncontrolled factors affecting deposition and eventual bioavailability.

SUMMARY

Briefly described, embodiments of this disclosure include systems and methods of particle detection in an inhaler. One exemplary system, among others, includes an ejector that ejects medicated droplets during an activation event, a conduit fluidically coupled to the ejector and configured to transport the droplets to a patient during an in-breath, and a particle detection system configured to determine whether the droplets have properly passed through the conduit and to the patient during an activation event.

In another exemplary embodiment, the inhaler system includes the following: an inhaler housing; a conduit disposed within the inhaler housing configured to support particle flux therethrough; an inhaler control system disposed within the inhaler housing; a medicament supply system communicatively coupled to the inhaler control system, the medicament supply system including a medicament ejector; and a detection system positioned to allow detection of particles in the conduit.

One exemplary method, among others, includes: generating a dose of medicament particles from an inhaler system; detecting particles emitted in the inhaler system; and determining if a desired particle flux has been achieved for inhalation by a patient.

BRIEF DESCRIPTION OF THE DRAWINGS

Many aspects of this disclosure can be better understood with reference to the following drawings. The components in the drawings are not necessarily to scale. Moreover, in the drawings, like reference numerals designate corresponding parts throughout the several views.

FIG. 3 illustrates an alternative embodiment of an inhaler system.

FIG. 4 illustrates an embodiment of a method of operating an inhaler system.

FIG. 5 illustrates an embodiment of a method of determining amount of uptake of medicament from an inhaler system.

DETAILED DESCRIPTION

Figure 1:
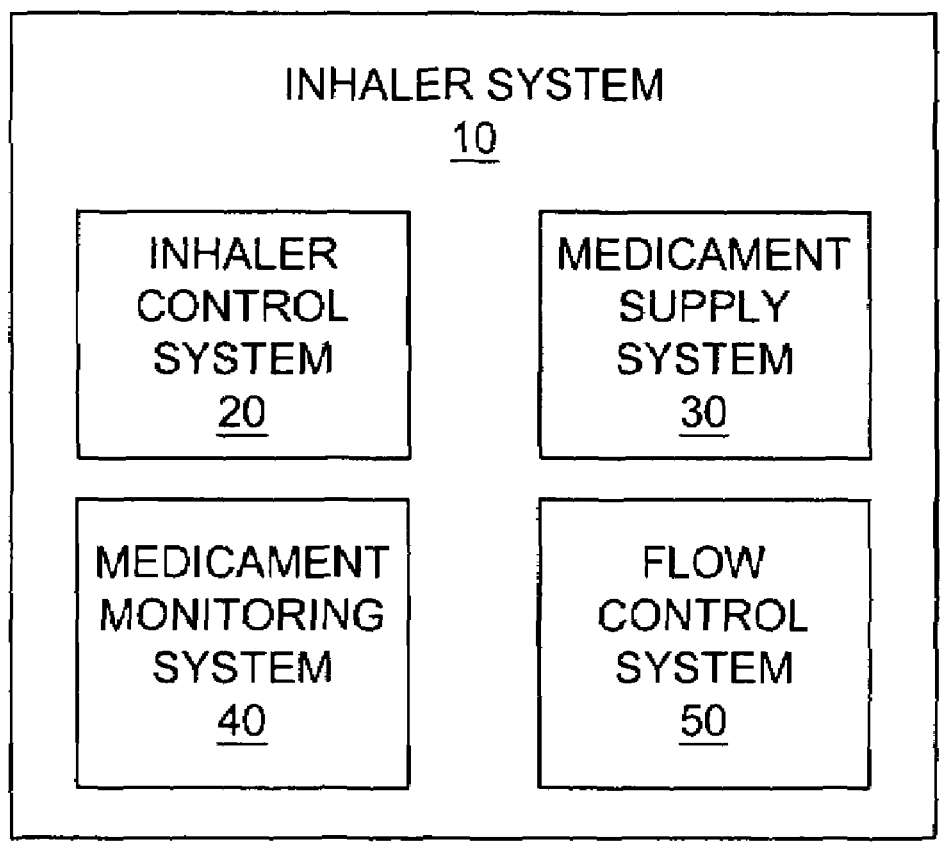
FIG. 1 illustrates an embodiment of an inhaler system.

Inhaler systems and methods of detecting inhaler particles in inhalers for verifying the integrity of delivery of doses are provided. In particular, embodiments relate to an electronically-controlled aerosol generator for delivering medicament to a patient's pulmonary system. With conventional inhalers, the actual uptake of medicament by a patient is generally unknown. The disclosed inhaler systems provide a more accurate and direct measurement of aerosol uptake by a patient. The disclosed inhaler systems include a particle detection system configured to provide an estimate of the particle flux (total number of particles per unit time) being delivered by the inhaler. The disclosed inhaler systems can also be configured to declare a fault, warning, or other annunciation if the patient fails to properly inhale the generated aerosol.

In general, the inhaler system includes a medicament ejector and a mouthpiece (e.g., an inhalation/exhalation structure) that are coupled by a conduit or a flow control system. In use, the patient first places the patient's mouth (or nose in some cases) on the mouthpiece and then takes an in-breath or inhales to receive the medicament (e.g., typically in the form of a medicated aerosol). Preferably, the patient also breathes out or exhales into the mouthpiece during an out-breath.

The medicament ejector includes a face having an array of nozzles or orifice for controllably ejecting medicated aerosol droplets. The medicament ejector is an electronically-controlled drop ejecting device that utilizes a drop generating device (e.g., a thermal bubble generator, a piezo drop generator, and a vibrating porous membrane) to generate droplets of the medicament, which can be entrained in the in-breath.

The conduit is configured to allow air to entrain the medicament droplets so that they pass to the mouthpiece during an in-breath. In other words, during the in-breath, the flow control system defines an "in-breath airflow path" or "an inhalation airflow" that carries the medicament droplets from the medicament ejector face to the mouthpiece. In addition, the flow control system includes an inlet port for receiving air during an in-breath. During the in-breath of a patient, air flows from the inlet port, past the medicament ejector (entraining the medicament aerosol), and to the mouthpiece along the in-breath airflow path.

The flow control system also defines an "out-breath airflow path" or "exhalation airflow" during the patient's out-breath. The out-breath airflow path does not retrace of the in-breath airflow path. By defining two different airflow paths, the flow control system impedes the flow of air from the mouthpiece to the medicament ejector during the out-breath of the patient. Thus, the out-breath airflow path substantially bypasses the medicament ejector to avoid contamination of the medicament ejector during the out-breath. The flow control system also includes an outlet port that is separated physically from the inlet port. During an out-breath of the patient, air flows from the mouthpiece to the outlet port substantially bypassing the medicament ejector. To provide added assurance that the out-breath air flow path does not substantially impinge upon and contaminate the medicament ejector, one or more valves (e.g., check valves or one-way valves) may be employed.

The disclosed inhalation system of this disclosure also includes a detection system that is configured to monitor the particle flux or particle density of medicated droplets as they pass through the conduit to the mouthpiece. Preferably, the detection system is configured to detect particles or a particle flux in a portion of the conduit that is spaced sufficiently far from the ejector face to differentiate between droplets ejected from the ejector and droplets properly passing through the conduit during the in-breath. In other words, the detection system is able to not only measure particles being generated, but also particles delivered along the conduit to and from the mouthpiece during an in-breath or an out-breath, respectively.

The inhalation system also includes system control electronics coupled to the ejector and the detection system. The control electronics activate the ejector to generate medicated droplets and receive signals from the detection system indicative of the particle flux or density. The control electronics analyze the signals to determine if the proper flux of medicated droplets has been delivered along the conduit during an in-breath. If this flux differs enough from an expected flux, a fault can be declared that is followed by another action. Examples of another action include warning the patient that the medication has not been properly delivered or shutting down the ejector.

The control electronics can also analyze the signals during the out-breath to determine the particle flux that the patient breaths out and to determine a net dosage delivered. The net dosage absorbed by the patient, otherwise referred to as the uptake of the medication, can be estimated by a total number of particles passing during an in-breath and a total number of particles passing during an out-breath. The control electronics analyzes this information to determine more accurately whether a proper net dosage of medication has been absorbed. If the net dosage is too low, the control electronics activates a device such as, for example, a light-emitting device, an audio device, or a display message signaling the user to take additional inhalations.

In a preferred embodiment, the control electronics include a calibration factor stored in non-volatile memory. The control electronics uses the calibration factor to compute the amount of droplets to eject in order to achieve a given uptake. Stated another way, the calibration factor correlates the expected amount of medication to be absorbed as a function of the total number of droplets to be ejected by the ejector.

In a preferred embodiment, control electronics uses the comparison between the particles passed during an in-breath and an out-breath to adjust the calibration factor. This will tend to vary from patient to patient even in the case of various patients who properly use the inhalation device. The control electronics can adjust this calibration factor so that future doses of delivered medicant more closely match the intended dosage. This can be used to minimize the number of inhalations required for a proper dose.

Turning now to the figures, FIG. 1 illustrates a block diagram of a representative inhaler system 10 that includes, but is not limited to, an inhaler control system 20, a medicament supply system 30, and a medicament monitoring system 40 for monitoring the amount of medicament inhaled and exhaled by the patient. In addition, the inhaler system 10 can include a flow control system 50.

In general, the inhaler control system 20, the medicament supply system 30, the medicament monitoring system 40, and in some instances the flow control system 50, are communicatively coupled to function together to control the release of the medicament and the airflow caused by inhalation out of and exhalation into the inhaler system 10. In practice, the patient inhales on an inhalation/exhalation structure of the inhaler system 10 and depresses a button or switch to cause the medicament to be released. As the patient inhales on the inhaler system 10, the flow control system 50 causes inhalation airflow to pass across the structure releasing the medicament. Once the button is activated, the medicament flows with the inhalation airflow into the patient. After inhalation, the patient exhales into the inhaler system 10. Then the optional flow control system 50 can redirect the exhalation airflow away from the structure that releases the medicament, which substantially decreases the likelihood of contaminating the medicament releasing structure. In addition, during the inhalation and exhalation, the medicament monitoring system 40 is used to monitor the amount of medicament being inhaled by the patient.

The inhaler control system 20 includes, but is not limited to, a computer system and a mechanical system, both of which activate/deactivate the medicament supply system 30. The computer system can include, but is not limited to, programmable logic circuits (e.g., a microprocessor) to control the quantity of medicament released by the medicament supply system 30. The mechanical system can include, but is not limited to, an actuation structure (e.g., button or switch), a spring mechanism in communication with the actuation structure, and similar components used to communicate that the patient is requesting medicament release.

The medicament supply system 30 can be activated by the patient depressing the actuation structure in an effort to release the medicament and/or indicate that the patient is ready to receive the medicament. The medicament supply system 30 includes, but is not limited to, a medicament container and a medicament ejector. The inhaler control system 20 in conjunction with the medicament supply system 30 releases a known amount of the medicament from the medicament container and through the medicament ejector. Once the medicament is released, the flow control system 50 uses the inhalation airflow to carry the medicament to the patient during inhalation. During exhalation, the flow control system 50 directs the exhalation airflow away from the medicament ejector. The flow control system 50 includes, but is not limited to, one or more inhalation/exhalation valves such as a one-way valve (e.g., a valve in which airflow can proceed in one direction or else the valve closes) and channels. The inhalation/exhalation valves control the airflow through the inhaler system 10 by opening and closing under certain conditions. For example, one inhalation/exhalation valve opens during inhalation while another inhalation/exhalation valve closes. In this instance, the inhalation airflow is controlled by the opening and closing of particular inhalation/exhalation valves. In addition, the opening and/or closing of the inhalation/exhalation valves can be used to activate/deactivate of the medicament supply system 30.

The activation/deactivation of the medicament supply system 30 can be controlled based on information from the medicament monitoring system 40. For example, the medicament monitoring system 40 is adapted to determine if the patient inhaled a threshold amount of the medicament, desirably by employing the disclosed method(s). Based on this determination by the medicament monitoring system 40, the inhaler control system 20 can alert (e.g., an audible and/or visual signal) the patient whether or not the inhalation was successful.

Figure 2:
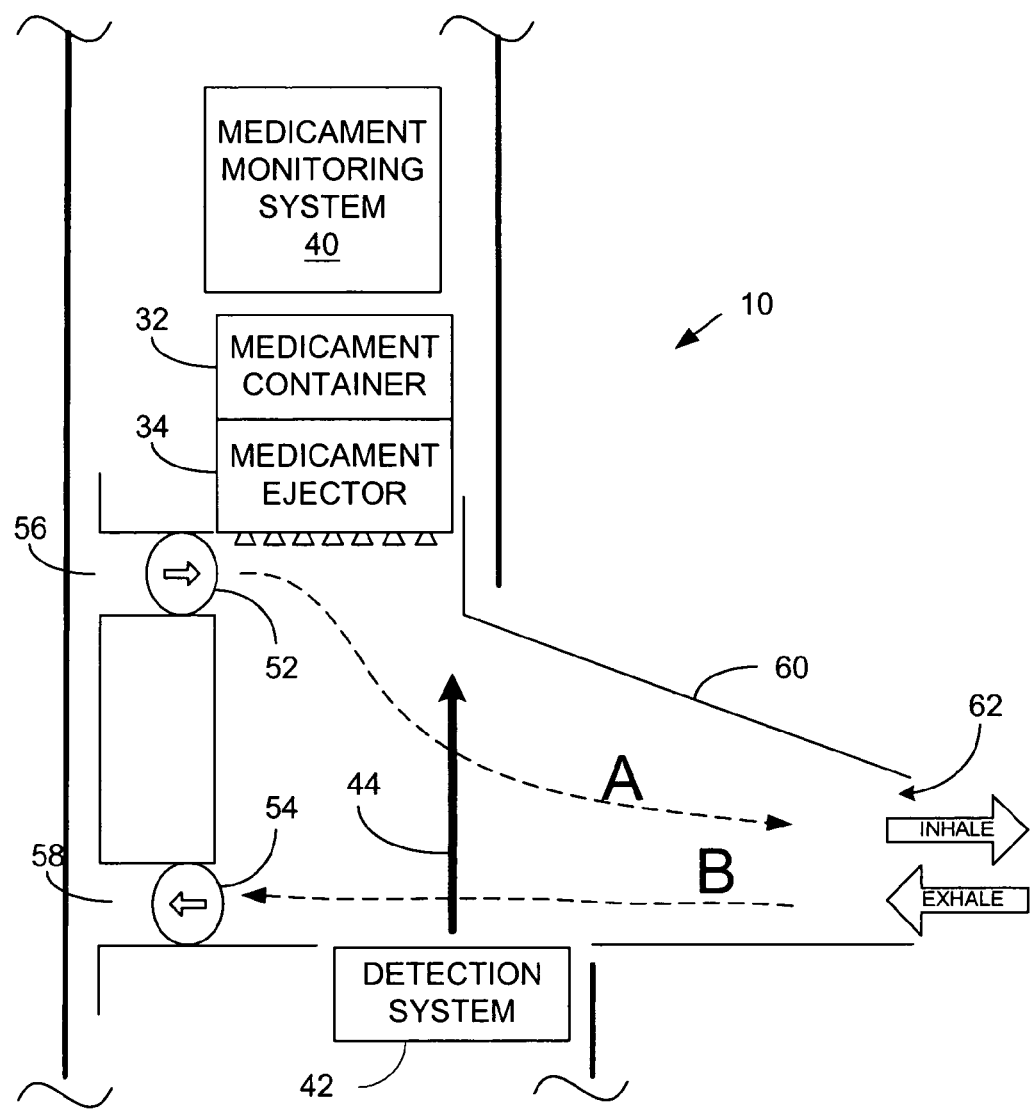
FIG. 2 illustrates an embodiment of a inhaler particle detection system incorporated into the inhaler system of FIG. 1.

Now having described the inhaler system 10 in general, FIG. 2 illustrates an exemplary embodiment of the inhaler system 10. This example is not intended to limit the scope of any embodiment of this disclosure, but rather is intended to provide a representative embodiment. Therefore, one skilled in the art would understand that the components of the inhaler system 10 and the configuration of the components within the inhaler system 10 can be modified, and it is intended that any such modifications be within the scope of the embodiments of this disclosure.

FIG. 2 depicts a simplified pictorial block diagram of a representative inhaler system 10. The inhaler system 10 includes a medicament container 32 for housing the medicament and a medicament ejector 34, which are parts of the medicament supply system 30. The medicament ejector 34 can include, but is not limited to, a piezoelectric type device and thermal bubble jet device, to eject the medicament. The various types of medicament containers 32 and the medicament ejectors 34 are known in the art (e.g., U.S. Pat. No. 5,894,841) and are not described in additional detail here.

The inhaler system 10 also includes an inhalation/exhalation structure 60 (e.g., an inhalation/exhalation mouthpiece) having an inhalation/exhalation orifice 62. The inhalation/exhalation orifice 62 is the point at which the patient contacts the inhaler system 10 to breathe out of and into the inhaler system 10. The inhalation/exhalation structure 60 can be a permanent part of the inhaler system 10 or it can be a removable and replaceable part of the inhaler system 10. The inhalation/exhalation structure 60 can have various designs and be made of various materials.

The inhaler system 10 also includes a detection system 42, which is part of the medicament monitoring system 40. The detection system 42 can be located a various positions within the inhaler system 10 to monitor the medicament flow into and out of the inhaler system 10. The detection system 42 can include, but is not limited to, at least one laser system and at least one laser detector. In practice, the laser system emits laser light 44 during inhalation and exhalation, while the laser detector detects laser light scattered by the medicament passing along the path of the laser light.

The inhaler system 10 also includes a flow control system 50 in fluidic communication with the medicament ejector 34. The flow control system 50 is adapted to control the airflow (inhalation airflow A and exhalation airflow B) within the inhaler system 10. In particular, the flow control system 50 causes inhalation airflow A to pass across the medicament ejector 34. Therefore, as the patient breathes in (e.g., causing the inhalation airflow A to flow out of the inhaler system 10) and depresses the actuation structure to release the medicament, the inhalation airflow A carries the medicament through the inhalation/exhalation structure 60 and into the patient's lungs. After inhalation, the patient exhales into the inhaler system 10. The flow control system 50 redirects the exhalation airflow 74 away from the medicament ejector 34, which substantially decreases the likelihood of contaminating the medicament ejector 34.

The flow control system 50 includes, but is not limited to, at least inhalation valve 52 and an exhalation valve 54. The inhalation valve 52 and an exhalation valve 54 can be the same type of valve or different types of valves. The inhalation valve 52 and/or the exhalation valve 54 can be selected from, but is not limited to, a one-way valve, a check valve, a flapper valve, and combinations thereof.

In addition, the flow control system 50 includes an inlet port 56 in fluid communication with the inhalation valve 52 and an outlet port 58 in fluid communication with the exhalation valve 54. As the patient inhales, the inhalation valve 52 opens and air flows through the inlet port 56 into the inhaler system 10. As the patient exhales, the exhalation valve 54 opens and air flows through the outlet port 58 out of the inhaler system 10.

The inhalation valve 52 is disposed adjacent the medicament ejector 34, while the exhalation valve 54 is disposed away or spaced from the medicament ejector 34. The position of the inhalation valve 52 is selected so that upon the inhalation breath, the inhalation airflow A passes over the medicament ejector 34. In this manner, the medicament is carried through the inhalation/exhalation structure 60 and orifice 62 and into the patient. The position of the exhalation valve 54 is selected so that upon the exhalation breath, the exhalation airflow B does not substantially pass over the medicament ejector 34. The inhaler system 10 (e.g., positions of the inhalation valve 52 and the exhalation valve 54) is desirably configured to limit the contamination of the medicament ejector 34. However, one skilled in the art could design the flow control system 50, the medicament ejector 34, and other components of the inhaler system 10 in a different manner as that shown in FIG. 2 to accomplish limiting the contamination of the medicament ejector 34.

The inhaler system 10 preferably further includes the medicament monitoring system 40 that can perform the disclosed methods, detailed below, for estimating delivered pulmonary doses. The medicament monitoring system 40 also can, based on information received from the detection system 42, signal to the inhalation control system 20 to vary a number of different pulmonary delivery parameters so as to optimize the dose received by the patient and/or reduce the variance between doses. The inhaler system 10 may include many other features and components not shown or described herein. For example, the inhaler system 10 may include a droplet generator, a dispersion chamber, and/or a feedback unit.

The flow control system 50 can be communicatively coupled with the inhaler control system 20, the medicament supply system 30, and the medicament monitoring system 40 to effectively release the medicament. For example, the patient may depress the actuation structure to release the medicament, but exhale instead of inhale. Since the inhalation valve 52a only opens upon inhalation and/or the exhalation valve 54 only opens during the exhalation, the flow control system 50 can be configured to communicate with the inhaler control system 20 and/or the medicament supply system 30 when these valves are open and/or closed. Therefore, medicament is not released during patient exhalation.

Figure 3:
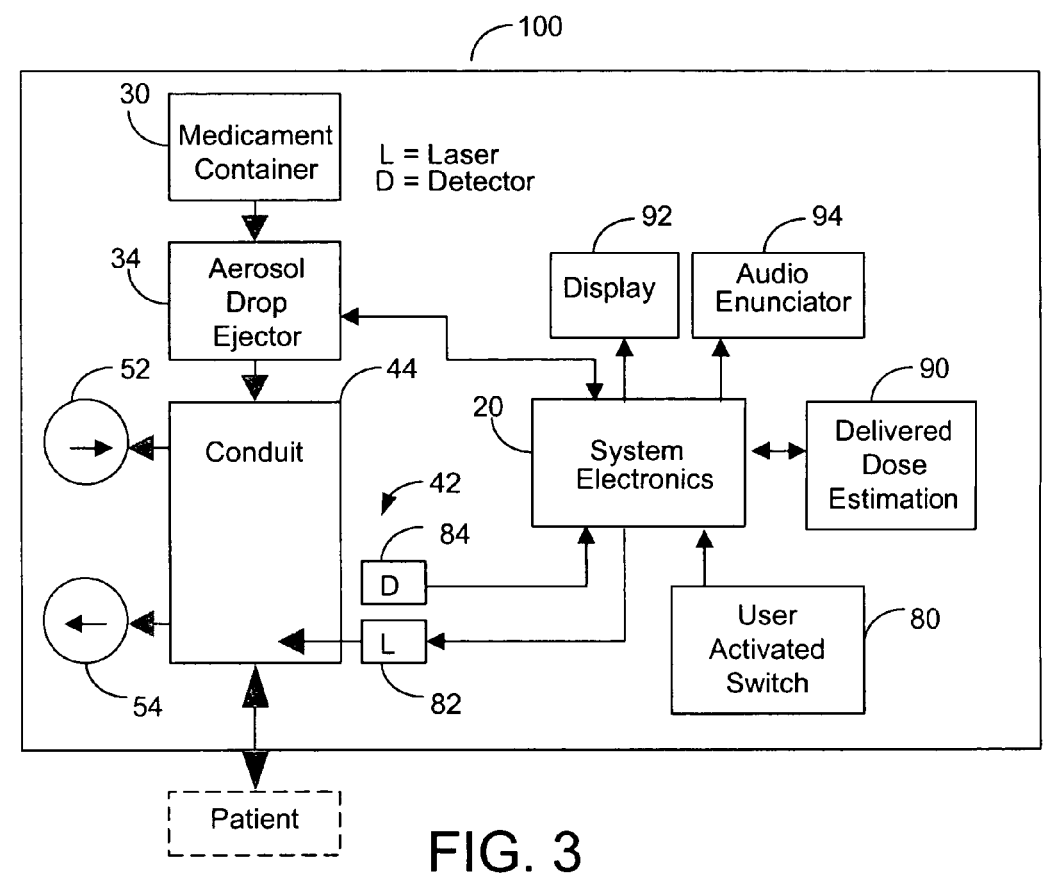
Figure 6:
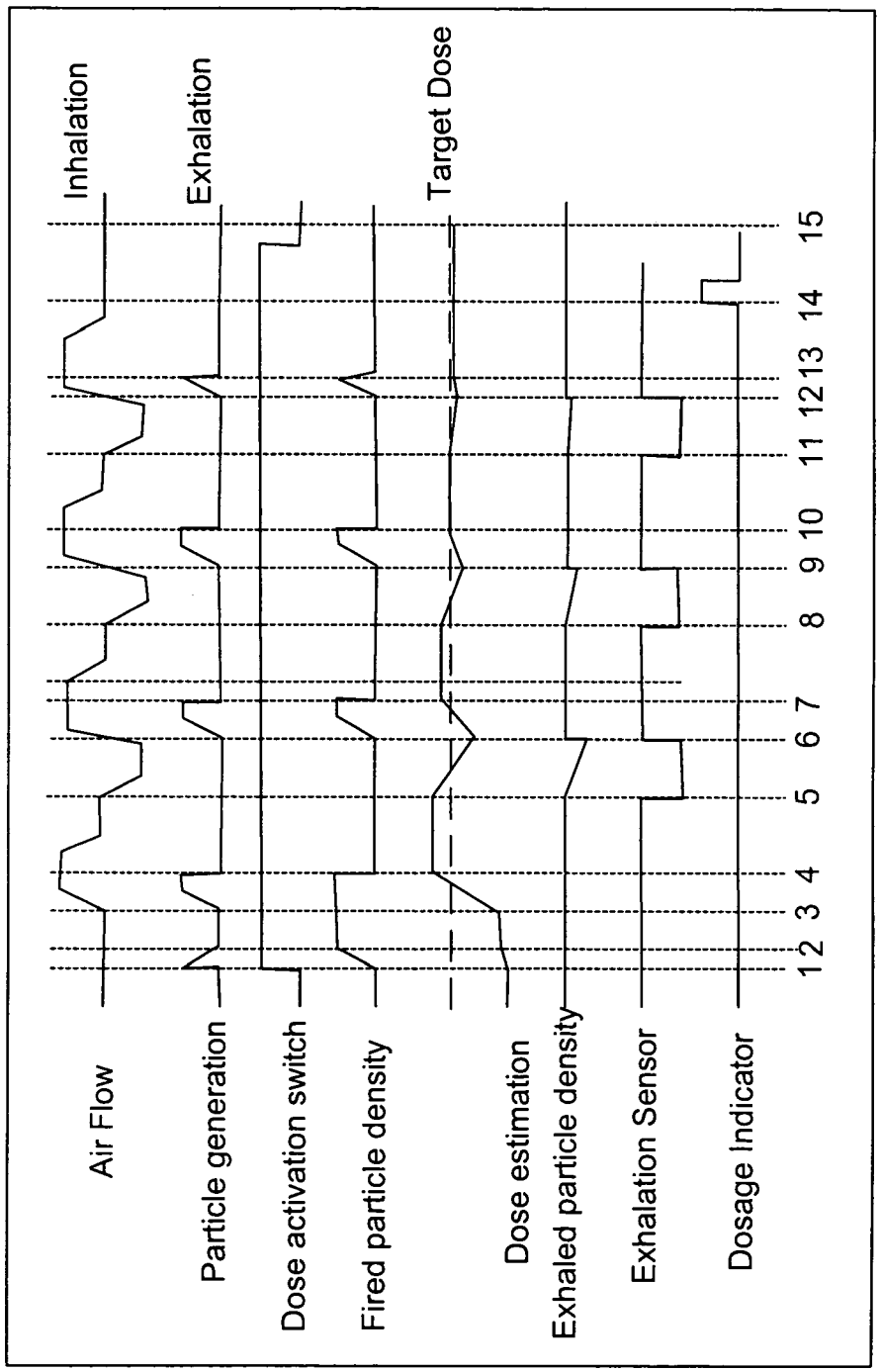
FIG. 6 illustrates a timing diagram when practicing an embodiment of a method of FIG. 5.

Shown in FIG. 3 is a simplified block diagram of an alternative embodiment of the disclosed inhaler system, depicted as inhaler system 100. A drop ejection device 34 such as a drop on demand jetting device (e.g., a piezo- or thermal-activated drop generator) is controlled by system electronics, also called the inhaler control system 20. The inhaler system 100 delivers medicament to a patient's pulmonary system via a conduit system 44, for example, an aerosol conduit system. Disposed in or adjacent the conduit system 44 is a detection system 42 that measures particle flux moving through the conduit system 44. The detection system 42 is desirably positioned to not only allow detection of particles but to also differentiate, based on whether the patient properly takes an in-breath during aerosol formation. As indicated previously, the detection system may include a laser device 82 and a detector 84.

Illustrated in FIG. 4 is a flow diagram of a representative method 200 of verifying the integrity of an inhaled dose. Generally, the flow chart illustrates the use of the disclosed inhaler system to determine proper uptake of a medicament. In the method 200 shown in FIG. 4, the particle detector is used to measure the integrated particle flux over time for in-breath by a patient, but it can be envisioned that the same method could be employed to measure both in-breath and out-breath. By comparing these values, the total dosage delivered to the pulmonary system can be inferred.

As shown in block 210 of FIG. 4, a patient initially activates the device (e.g., via a manual switch) and begins inhalation. Desirably, inhalation begins just prior to the patient activating the device. As shown in block 220, in response to the activation, the device begins aerosol generation and, shown in block 230, activates the particle detection system. As shown in block 240, the inhalation may also optionally start after the particle detection device is activated. At a certain threshold time, as shown in decision block 250, the system determines whether a proper particle flux has been detected. This would be the case if the patient is taking a proper in-breath. If a patient has taken a proper in-breath and a desired particle flux is obtained, the aerosol generation stops, as shown in block 260. At that point the patient begins to exhale, as shown in block 270.

If a patient has not taken a proper in-breath, then a "fault" is inferred, as depicted in block 280 and a fault response is desirably indicated to the patient, as shown in block 290. In the case fault, the device may have several possible responses. In an exemplary embodiment, the fault response comprises waiting for the aerosol to settle, giving a visible or audible alert to the patient that another dose required. The inhaler system can then proceed for readying itself for the patient to take the next dose.

FIG. 5 is a flow diagram of an alternative embodiment of the disclosed method of verifying the amount of medicament inhaled by a patient. In the method 300 of FIG. 5, the step of calibration is included. The disclosed inhaler system uses any shortfall in the first delivered dose to compute an increase in the amount of inhalant to be ejected relative to the targeted delivery for subsequent dose(s).

As shown in block 310 of FIG. 4, a patient initially activates the device (e.g., via a manual switch) and begins inhalation. As shown in block 320, in response to the activation, the device begins aerosol generation and, shown in block 330, activates the particle detection system. As shown in block 340, the inhalation may optionally begin after the particle detection device is activated. Aerosol generation stops, as shown in block 350, and then the patient exhales back into the inhaler system, as shown in block 360.

As part of activating the particle system, a means of tracking amount of aerosol is activated. This could take various forms, depending on the ejector mechanism employed. In the case of a thermal bubble or piezo-based drop ejector, the total number of drop generator actuations is controlled to provide the correct dose. For many cases the number of actuations are selected so that the calculated dose is at or below the expected dose. Alternatively, the time of actuation can be controlled, as would be preferable for a system such as a vibrating porous membrane. Again, the ejection time would be selected to deliver the proper dose.

Another aspect of activating the particle system is a calibration factor. In a non-volatile memory the system stores information indicative of a quantified relationship between a dosage delivered or absorbed and the number of droplets generated (or total time of activation). This information can be considered to be a calibration factor that may, for example, be a linear multiplier or a constant for a non-linear relationship between number of drops and quantity of medication absorbed. The control electronics uses this factor to calculate the proper time or number of drop generator actuations to provide the proper dose to the patient.

While the dosage is being delivered, and during exhalation, the particle detection remains active and acquiring information indicative of the total number of particles or droplets delivered through the conduit to the patient and preferably even the total number of particles or droplets that are exhaled. Based upon this information, the system can determine whether a full dose has been delivered and absorbed by the patient according to block 370. If the dose is correct, the inhalation process ends and the patient may receive an indication ("dose complete" message or the like) that the dosage is complete.

If the dosage is not correct, it would typically be too low. The patient receives an indication of this according to step 390. The patient can take another dose starting with the device activation step 310. This process would continue until the required dosage is achieved.

Assuming that the ejector is functioning properly, the dosage may not be correct for one or both of two reasons: (1) the patient has not inhaled properly or (2) the patient exhaled more medicated particles than expected. With the particle detection during inhalation, reason (1) can be identified and quantified. With the particle detection during exhalation, reason (2) can be identified and quantified. With reason (2), the patent is not absorbing enough medication even though the proper quantity of medicated droplets are being passed through the conduit. In the case of reason (2), the calibration factor is adjusted to more properly attain correct absorbed dosage. This will tend to reduce the number of times the patient has to inhale in order to get the proper dose.

In this way, the disclosed inhaler system becomes more accurate with dosages as the uptake is characterized. The disclosed inhaler system can learn from previous uptakes versus outputs from the patient. Thus, fewer inhalations may be required by the patient over time for a give dose.

Depicted in FIG. 6 is a timing diagram that illustrates the timing of an exemplary embodiment of a disclosed method, showing various aspects of the disclosed inhaler system in use. At step 1, the inhaler system is turned on, the particle density sensor detects low particle count, particle generation is initiated, and delivered dose estimation begins. At step 2, the particle density detector reaches density level set point, deactivating particle generation. At step 3, the patient begins inhaling, and the particle sensor detects a decrease in particle density and signals the particle generator to produce particles at a rate necessary to maintain set point particle density. At step 4, a dose estimation subsystem calculates that the delivered dose has reached some set point level above the target deposited dose and stops particle generation while the patient continues to inhale and then holds breath. At step 5, the patient begins to exhale, activating the exhalation sensor and causing the exhaled particle density sensor to begin accumulating signal. At step 6, the exhalation sensor is inactivated, the deposited dose subsystem deposited dose estimate is below the set point, and the particle density detector is below its set point value, causing particle generation to start. At step 7, the next delivered dose set point is reached, causing particle generation to cease while the patient continues to inhale and hold breath.

In step 8, as in step 5, the patient begins to exhale, activating the exhalation sensor and causing the exhaled particle density sensor to begin accumulating signal. In step 9, as in step 6, the exhalation sensor is inactivated, the deposited dose subsystem deposited dose estimate is below the set point, and the particle density detector is below its set point value, causing particle generation to start. In step 10, the next delivered dose set point is reached, causing particle generation to cease while the patient continues to inhale and hold breath. In step 11, as in steps 5 and 8, the patient begins to exhale, activating the exhalation sensor and causing the exhaled particle density sensor to begin accumulating signal. In step 12, as in steps 6 and 9, the exhalation sensor is inactivated, the deposited dose subsystem deposited dose estimate is below the set point, and the particle density detector is below its set point value, causing particle generation to start. In step 13, the final delivered dose set point is reached, causing particle generation to cease while the patient continues to inhale and hold their breath. In step 14, the patient continues to inhale and hold breath until an audio signal indicates that dosing is complete. In step 15, the patient deactivates the dose activation switch.

Figure 7:
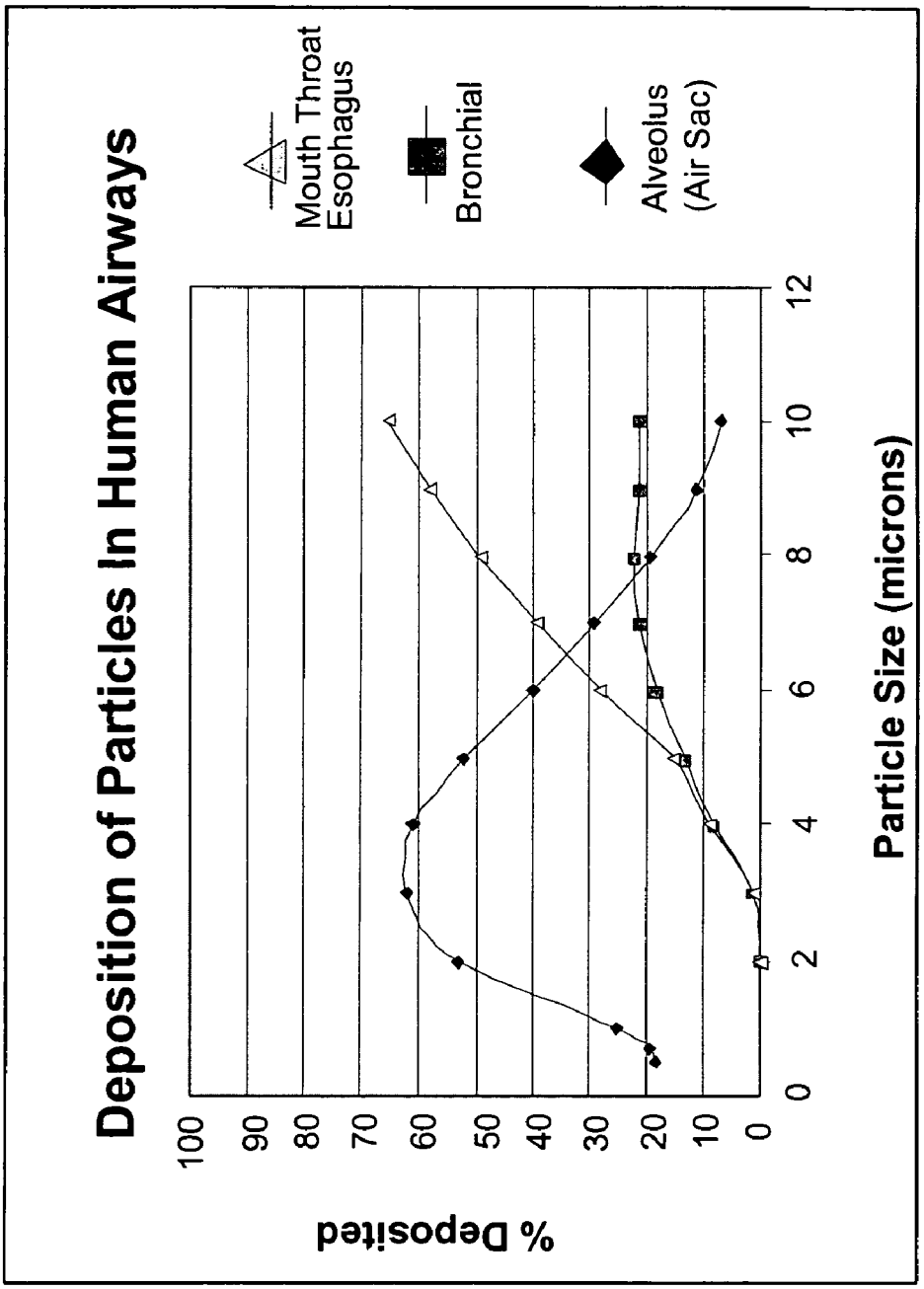
FIG. 7 illustrates the percentage deposition amounts of a medicament for a range of particle sizes, as measured by an embodiment of a disclosed inhaler system.

In the disclosed inhaler systems and methods, it may be desirable to use a medicament for inhalation that has particle sizes in the range of about 1 to 8 microns. It may also be desirable to use a medicament for inhalation that has a particle sized in the range of about 1 to 6 microns to achieve certain deposition of particles in the deep lung tissue. It may be preferred to use a medicament for inhalation that has a particle sized in the range of about 2 to 5 microns to achieve certain deposition of particles in the deep lung tissue, as depicted in the graph of FIG. 7, measured for a representative inhaler system disclosed herein.

Figure 8:
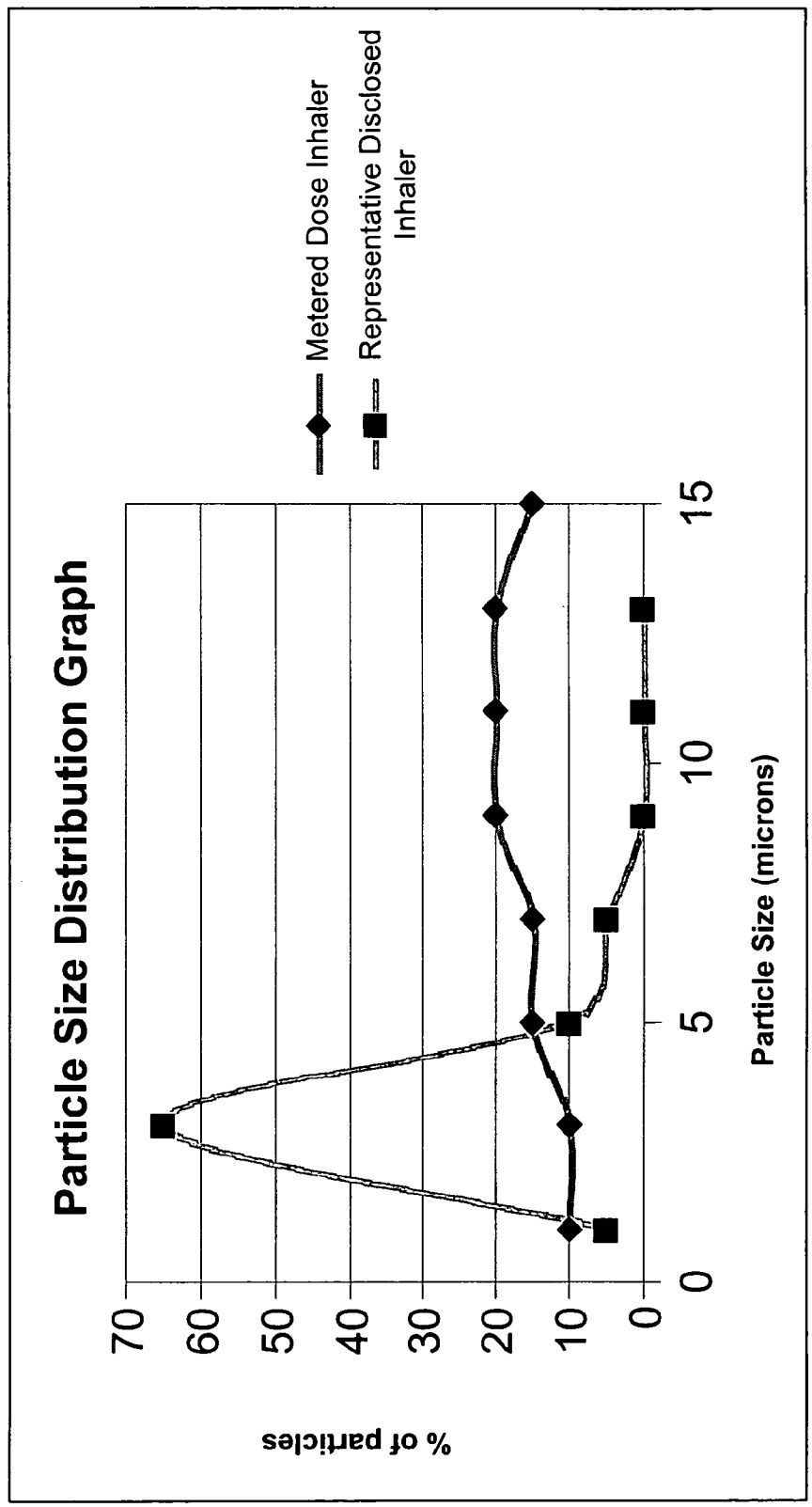
FIG. 8 is a chart of the particle size distribution produced by an embodiment of the disclosed inhalation system compared to a typical metered dose inhaler.

Preferably, the disclosed inhaler system creates a very narrow range of particles sizes as shown in FIG. 8, which aids in accuracy of the laser scatter method of particle detection. The laser scatter method can measure particle size distribution in some careful configurations but it can be difficult to measure both particle size distribution and absolute particle flux. For example, in a portable embodiment of the disclose inhaler system, a particle size distribution will probably be assumed and the particle count then used to compute the delivered volume. Error can arise as the various particle sizes have different deposition efficiencies. A narrow particle distribution should reduce the error inherent in these assumptions and computations.

The disclosed inhaler systems and methods allows for a more direct and accurate way to verify that a patient has received a proper dosage of inhalant. In particular, the disclosed methods allow the disclosed inhaler systems to determine whether a patient's in-breath has properly drawn in the desire amount of a dose of inhalant. Further, the disclosed methods allow the disclosed inhaler systems to estimate the amount of medicament exhaled by the patient's out-breath in order to further estimate the need for additional dosages.

Many variations and modifications may be made to the above-described embodiments. All such modifications and variations are intended to be included herein within the scope of this disclosure and protected by the following claims.

The invention claimed is:

1. An inhaler system, comprising:
   an inhaler housing;
   a conduit disposed within the inhaler housing configured to support particle flux therethrough;
   an inhaler control system disposed within the inhaler housing;
   a medicament supply system communicatively coupled to the inhaler control system, wherein the medicament supply system includes a medicament ejector; and
   a detection system positioned to allow detection of particles in the conduit, wherein the detection system is adapted to differentiate between particles being inhaled by a patient and particles being exhaled by the patient.

2. The inhaler system of claim 1, further comprising at least one of the following components disposed within the housing: a display, an audio enunciator, and an activation switch.

3. The inhaler system of claim 1, further comprising at least one indicator communicatively coupled to the detection system, wherein the indicator is configured to alert a patient if the patient has not inhaled a desired dosage amount.

4. The inhaler system of claim 1, wherein the detection system includes:
   a laser disposed downstream from the medicament ejector, and
   a detector that detects the particles scattered by the laser.

5. The inhaler system of claim 1, wherein the detection system further includes a timer that is configured to communicate with the laser and detector to measure particle flux.

6. The inhaler system of claim 1, wherein the medicament ejector has an ejector face, the detection system configured to detect particles in a portion of the conduit, the portion is spaced sufficiently far from the ejector face to differentiate between droplets ejected from the medicament ejector and droplets properly passing through the conduit during the in-breath.

7. The inhaler system of claim 1, further comprising a warning device for warning the user if the proper particle flux has not been delivered through the conduit.

8. The inhaler system of claim 7, wherein the warning device is selected from the group consisting of: a light emitting device, an audible device, and a display device.

9. The inhaler system of claim 1, wherein the inhaler control system includes control electronics coupled to the medicament ejector and the detection system, the control electronics configured to respond in the event that the droplets have not passed through the conduit during an activation event.

10. An inhalation system comprising:
an ejector that ejects medicated droplets during an activation event;
a conduit fluidically coupled to the ejector and configured to transport the droplets to a patient during an in-breath;

a particle detection system configured to determine whether the droplets have properly passed through the conduit and to the patient during an activation event;

an information storage device storing calibration information indicative of a correlation estimation between medication absorbed by a patient versus a number of drops ejected from the ejector; and control electronics coupled to the ejector and the detection system, wherein the control electronics utilize the calibration information to select a number of drops to be ejected, and the control electronics updates the calibration information based on information received from the particle detection system.

11. An inhalation system comprising:

an ejector that elects medicated droplets during an activation event;

a conduit fluidically coupled to the ejector and configured to transport the droplets to a patient during an in-breath;

a particle detection system configured to determine whether the droplets have properly passed through the conduit and to the patient during an activation event; and an inhaler control system communicatively coupled to the particle detection system and adapted to adjust at least one delivery parameter of the inhalation system, whereby the difference between desired dose and estimated delivered dose is reduced.

12. The inhalation system of claim 11, wherein the inhaler control system signals to the patient to increase the residence time of the particulate in the patient's lungs.

13. A method, comprising the steps of:

generating a dose of medicament particles from an inhaler system;

detecting particles emitted in the inhaler system;

determining if a desired particle flux has been achieved for inhalation by a patient detecting particles exhaled into the inhaler system by the patient; and determining if a desired amount of dose of medicament has been delivered to a patient.

14. The method of claim 13, further comprising the step of ceasing the generation of medicament particles if a desired particle flux has not been achieved.

15. The method of claim 13, further comprising the step of indicating a fault to the patient if a desired particle flux has not been achieved.

16. The method of claim 15, further comprising the steps of:

waiting for the particles to settle; and indicating to the patient that another dose of medicament particles may be taken.

17. The method of claim 13, further comprising the steps of:

the inhaler system calibrating itself to compensate for any shortfall in the amount of dose delivered to the patient; and generating a subsequent dose of medicament particles from an inhaler system.

18. The method of claim 13, further comprising the step of ceasing the generation of medicament particles if a desired amount of dose has been achieved.

19. The method of claim 13, further comprising the step of indicating a fault to the patient if a desired amount of dose has not been achieved.

20. A method, comprising the steps of:

generating a dose of medicament particles from an inhaler system;

detecting particles emitted in the inhaler system;

determining if a desired particle flux has been achieved for inhalation by a patient; and adjusting at least one delivery parameter of the inhaler, whereby the difference between desired dose and estimated delivered dose is reduced.

21. A method , comprising the steps of:

generating a dose of medicament particles from an inhaler system;

detecting particles emitted in the inhaler system;

determining if a desired particle flux has been achieved for inhalation by a patient; and adjusting at least one delivery parameter of the inhaler, whereby variance between estimated delivered doses to the patient is reduced.

22. A method, comprising the steps of:

generating a dose of medicament particles from an inhaler system;

detecting particles emitted in the inhaler system; and determining if a desired particle flux has been achieved for inhalation by a patient;

wherein the method is a feedback to an inhaler system controller that makes adjustments to delivery parameters based on the estimated delivered dose.

23. An inhaler system, comprising:

means for generating a dose of medicament particles from an inhaler system;

means for detecting particles emitted in the inhaler system;

means for determining if a desired particle flux has been achieved for inhalation by a patient;

means for indicating to patient that another dose of medicament particles may be taken;

means for detecting particles exhaled into the inhaler system by the patient; and means for determining if a desired amount of dose of medicament has been delivered to a patient.

24. The inhaler system of claim 23, further comprising means for ceasing the generation of medicament particles if a desired particle flux has not been achieved.

25. The inhaler system of claim 23, further comprising means for indicating a fault to the patient if a desired particle flux has not been achieved.

26. The inhaler system of claim 23, further comprising means for ceasing the generation of medicament particles if a desired amount of dose has been achieved.

27. An inhaler system, comprising:

means for generating a dose of medicament particles from an inhaler system;

means for detecting particles emitted in the inhaler system;

means for determining if a desired particle flux has been achieved for inhalation by a patient;

means for indicating a fault to the patient if a desired amount of dose has not been achieved;

means for calibrating the inhaler system to compensate for any shortfall in the amount of dose delivered to the patient; and means for generating a subsequent dose of medicament particles from an inhaler system.

* * * * *

UNITED STATES PATENT AND TRADEMARK OFFICE
CERTIFICATE OF CORRECTION

| | | |
|---|---|---|
| PATENT NO. | : 7,380,550 B2 | Page 1 of 1 |
| APPLICATION NO. | : 10/768865 | |
| DATED | : June 3, 2008 | |
| INVENTOR(S) | : Douglas A. Sexton et al. | |

It is certified that error appears in the above-identified patent and that said Letters Patent is hereby corrected as shown below:

In column 11, line 20, in Claim 11, delete "elects" and insert -- ejects --, therefor.

In column 12, line 13, in Claim 21, delete "method ," and insert -- method, --, therefor.

Signed and Sealed this

Second Day of December, 2008

JON W. DUDAS
*Director of the United States Patent and Trademark Office*